(12) United States Patent
Ziran et al.

(10) Patent No.: US 11,660,122 B2
(45) Date of Patent: May 30, 2023

(54) UNIVERSAL CLAMP APPARATUS FOR BONE FIXATION DEVICE

(71) Applicant: ADVANCED TRAUMA SOLUTIONS, LLC, Decatur, GA (US)

(72) Inventors: Bruce H. Ziran, Decatur, GA (US); Patrick Kelly Capeheart, Dahlonega, GA (US); Christian Lutz, Heikendorf (DE); Ole Prien, Kiel (DE); Roman Rau, Kiel (DE)

(73) Assignee: INFIX, INC., Tampa, FL (US)

( * ) Notice: Subject to any disclaimer, the term of this patent is extended or adjusted under 35 U.S.C. 154(b) by 0 days.

(21) Appl. No.: 17/524,285

(22) Filed: Nov. 11, 2021

(65) Prior Publication Data

US 2022/0296278 A1 Sep. 22, 2022

Related U.S. Application Data

(60) Provisional application No. 63/163,146, filed on Mar. 19, 2021.

(51) Int. Cl.
*A61B 17/64* (2006.01)
(52) U.S. Cl.
CPC ........ *A61B 17/6458* (2013.01); *A61B 17/645* (2013.01)
(58) Field of Classification Search
CPC . A61B 17/64; A61B 17/6466; A61B 17/6458; A61B 17/6475; A61B 17/6483; A61B 17/6416; A61B 17/642; A61B 17/6433; A61B 17/6441; A61B 17/645; A61B 17/62; E05B 83/10; E05B 1/0015; B25G 1/005; B25G 1/002; B25G 1/04; B25G 1/06; B25G 1/066; Y10T 403/7171; Y10T 403/7129; Y10T 403/7135; Y10T 403/7141

See application file for complete search history.

(56) References Cited

U.S. PATENT DOCUMENTS 4,620,533 A * 11/1986 Mears ................. A61B 17/645
606/54
5,947,671 A * 9/1999 Kanaan ................. G05G 1/10
74/555
9,155,560 B2 10/2015 Mingozzi et al.
(Continued)

*Primary Examiner* — Jan Christopher L Merene
*Assistant Examiner* — Allie D Cline
(74) *Attorney, Agent, or Firm* — Thomas | Horstemeyer, LLP

(57) ABSTRACT

A universal clamp apparatus for orthopedic external fixators is disclosed. Preferably, the universal clamp apparatus has two pin/rod clamps, each having seating grooves for attaching to a frame rod associated with a frame of the fixator and/or a bone pin for implantation in a bone fragment. A clamp screw extends through and connects the first and second pin/rod clamps. An ergonomically designed knob having at least one collapsible or non-collapsible turn lever acts as a torque amplifier when rotated by hand without tools to tighten and untighten the pin/rod clamps to the frame rod and/or bone pin by movement along the clamp screw. The pin/rod clamps have planar sides that are contiguous and have radial ratchet grooves that are in mating engagement and provide a ratcheting mechanism so that the rotation of the pin/rod clamps relative to each other occurs in incremental rotational steps.

20 Claims, 13 Drawing Sheets

(56) References Cited

U.S. PATENT DOCUMENTS

| | | | |
|---|---|---|---|
| 10,722,268 B2* | 7/2020 | Muniz | A61B 17/6416 |
| 2006/0287652 A1* | 12/2006 | Lessig | A61B 17/6458 |
| | | | 606/54 |
| 2019/0110814 A1* | 4/2019 | Nemovicher | A61B 90/57 |
| 2021/0100585 A1* | 4/2021 | Kent | A61B 17/6416 |

* cited by examiner

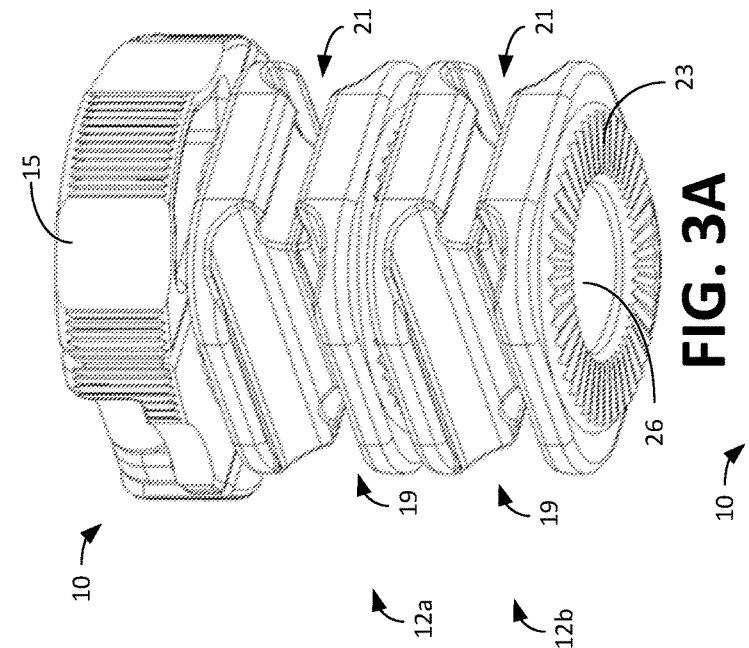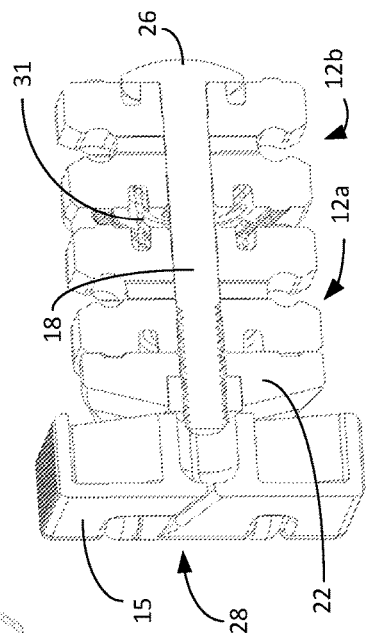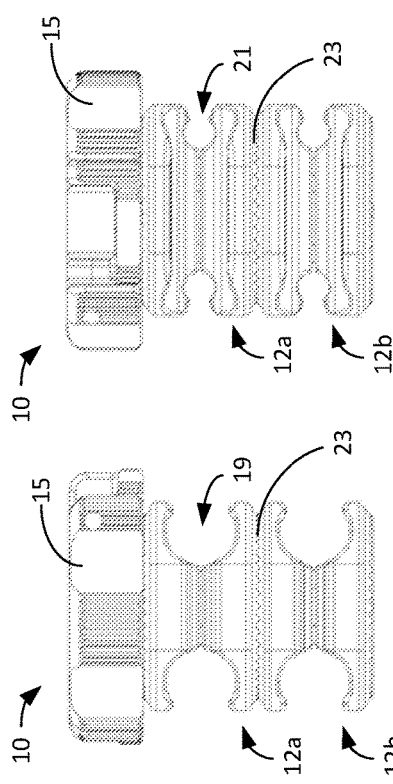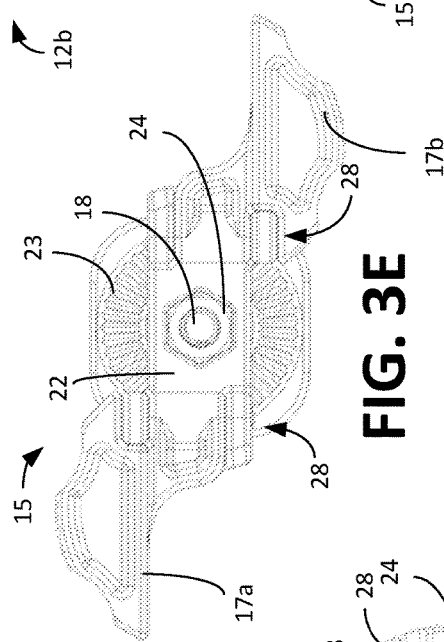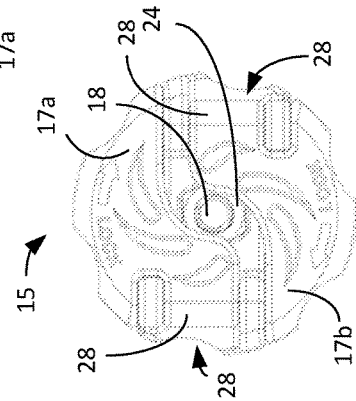

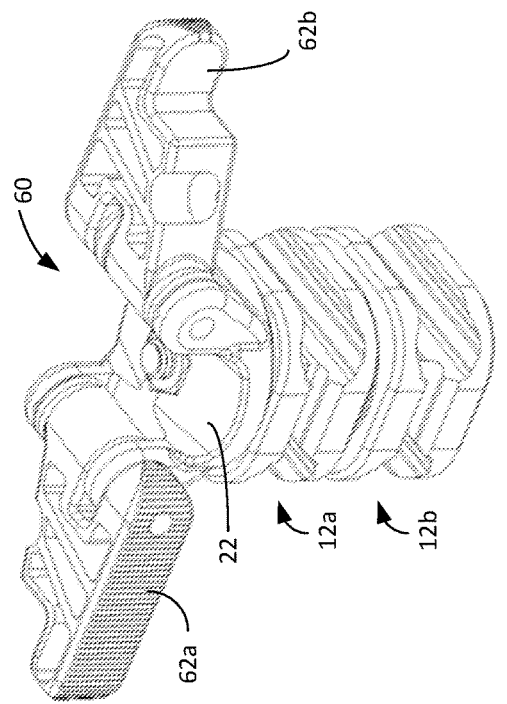
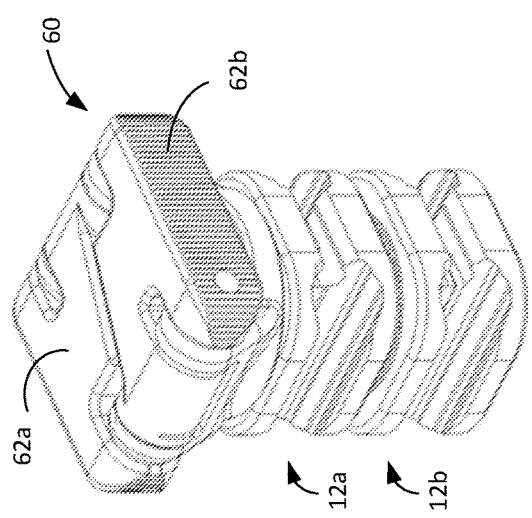
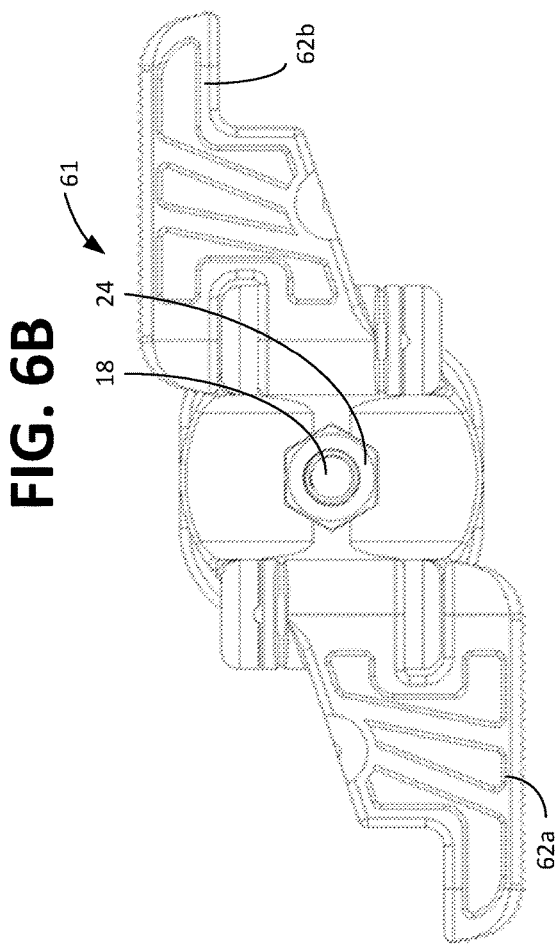
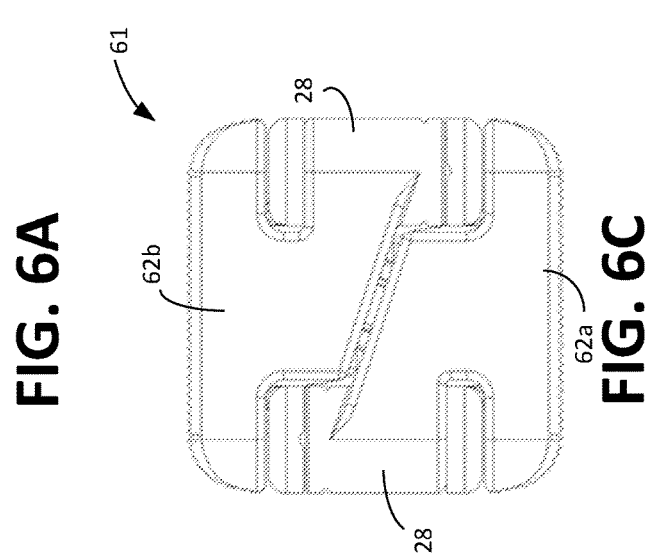
FIG. 6A
FIG. 6B
FIG. 6C
FIG. 6D

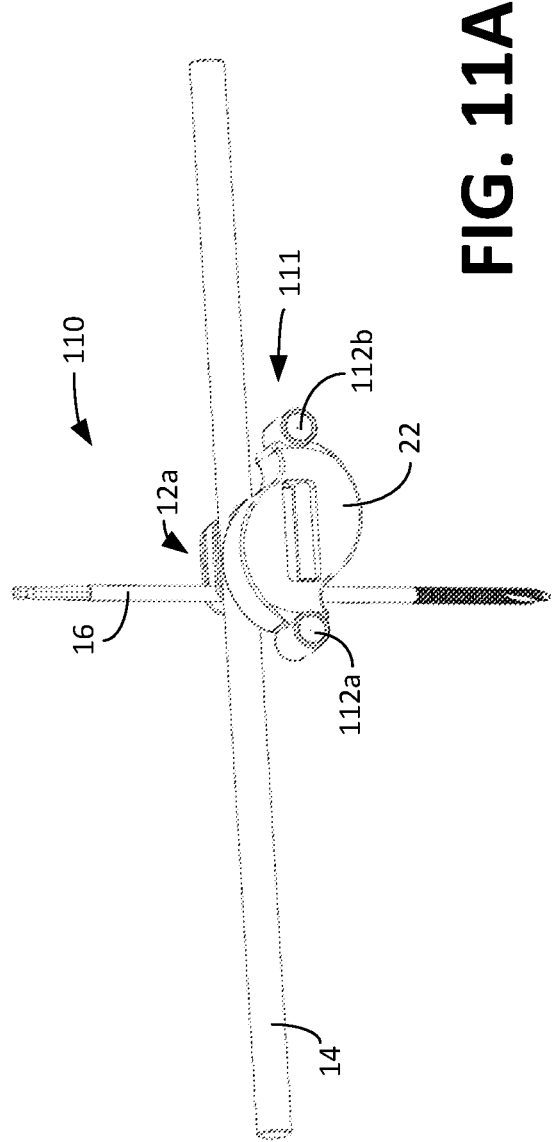
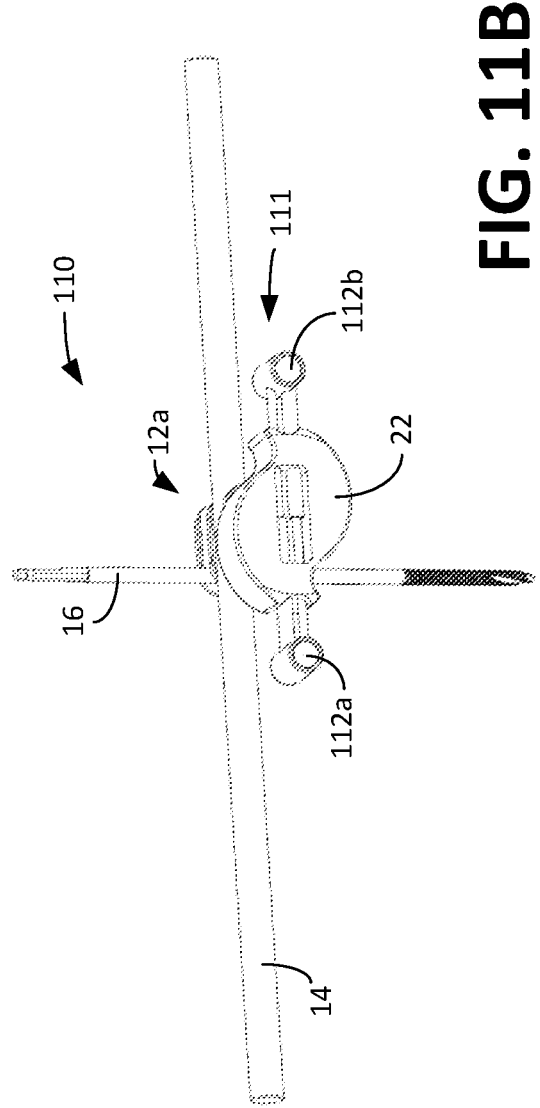

UNIVERSAL CLAMP APPARATUS FOR BONE FIXATION DEVICE

CLAIM OF PRIORITY

This application claims priority to and the benefit of provisional application No. 63/163,146, filed Mar. 19, 2021, which is entirely incorporated herein by reference.

FIELD OF THE INVENTION

The embodiments of the present disclosure generally relate to the medical field of fractures and deformity, and more particularly, to multi-purpose external fixators that are used for stabilizing fractures in patients.

BACKGROUND OF THE INVENTION

In the medical field of orthopedics, for several years a technique has been known for stabilizing fractures by using external fixators instead of conventional plaster casts. External fixators usually comprise a plurality of threaded bone pins, or screws, normally in pairs, which are implanted in the bone fragments of the fracture in such a way that the head ends of the bone pins project from the skin of the patient. The ends are anchored to a rigid external frame which is equipped with clamps and rods, which can be orientated in such a way as to allow them to be adjusted to the position of the bone pins.

The bone pins usually have a cylindrical body, delimited on one side by a threaded end designed to be screwed into the bone fragment, and on the other side by the above-mentioned head end, which is shaped in such a way that it can be connected to a temporary grip that allows the pin to be screwed into the bone fragment. The connection between the pin and the grip is normally of the male-female type with quick coupling and release or another conventional mechanical interface.

During its application the pins are placed on opposite sides of the fracture span and connect to a clamp that allows connectivity between pins. Then the surgeon connects the pins, clamps, and a series of bars together. If necessary, the surgeon then aligns the limb for either temporary or permanent positioning. In most cases, the alignment is also to stabilize the body part to prevent further damage, and allow transport to a different level of care, or to allow the injury to evolve and ultimately allow a safer invasive procedure (damage control, often called "reduction").

Once the fracture has been reduced, the surgeon locks the joints and clamps to hold the bone fragments in the predetermined position, thus allowing the correct alignment between the bone fragments, which through the formation of "bone callus", gradually restores the lamellar bone tissue with which the bone recovers its original continuity and functionality.

The use of external fixators was extended to a vast range of orthopedic operations, such as limb lengthening, correction of bone axis rotary and angular deformities, pseudarthrosis, etc. In other words, external fixators are today used as multi-purpose orthopedic devices, both to correct deformations caused by trauma and to correct pathological deformations.

U.S. Pat. No. 9,155,560, which is incorporated herein by reference, discloses an example, among others, of a multi-purpose external fixator that has a universal clamp apparatus. The universal clamp apparatus has parallel first and second clamps, each having a pair of channels, one that is sized to receive and attach to a rod associated with a frame of the fixator and another that is sized to receive and attach to a bone pin. A collapsible handle with cam mechanism is employed to selectively either secure or unsecure the frame rod and/or bone pin in the first and second clamps. When the handle is closed, the frame rod and/or bone pin are squeezed and secured in the respective channels. A primary disadvantage of this universal clamp apparatus is that when the handle is closed, the first and second clamps have an imprecise fixed degree of tightness with respect to the rod and/or bone pin. This results in an inability to properly secure the frame rod and/or bone pin as well as readjust the squeezing tightness, when necessary. Furthermore, there is a risk that the collapsible handle could catch an object and get loosened, thereby causing the clamp to lose stability.

Other fixators have utilized a progressive tightening, usually through the use of a compressive screw design. These fixators require the use of a "tool" such as a wrench to tighten and loosen the clamp. In the surgical arena, the tool is often part of a "set" of instruments that requires sterilization. Without the tool, the clamp tightening can be compromised, even when provisional texturing of the clamp allows some "hand tightening". When these fixators are used in austere environments (i.e. warfare, rural and underserved areas), the tool may be lost and the utility of the fixator is compromised.

SUMMARY OF THE INVENTION

Embodiments of a new universal clamp apparatus for a multi-purpose orthopedic external fixator and methods associated therewith are disclosed. Advantageously, the universal clamp apparatus can be operated without the need for tools and with extraordinary tightening precision. Furthermore, there is low risk that the universal clamp apparatus will lose stability, i.e., its grasp on the pin(s) and/or rods, in the event that it hits or catches on an object.

One embodiment, among others, of the universal clamp apparatus is described as follows. The universal clamp apparatus has a plurality of pin/rod clamps. Each pin/rod clamp has at least one seating groove for snapping in and attaching to at least one of the following: a frame rod associated with a frame of the fixator and a bone pin for implantation in a bone fragment associated with a patient. This enables each universal clamp to form the following attachments: pin to rod, rod to rod, and pin to pin. A threaded mechanism, for example, a clamp screw, extends through and connects the first and second pin/rod clamps. An ergonomically designed knob having at least one collapsible or non-collapsible turn lever that acts as a torque amplifier when rotated to tighten and untighten the pin/rod clamps to the frame rod and/or bone pin by movement of the pin rod clamps along the threaded mechanism. Planar sides of the pin/rod clamps that are contiguous each have radial ratchet grooves that are in mating engagement and that implement a ratcheting and securing mechanism so that the rotation of the pin/rod clamps relative to each other occurs in discrete incremental rotational steps.

Another embodiment, among others, of a universal clamp apparatus for an orthopedic external fixator is as follows. The universal clamp apparatus has first and second pin/rod clamps. Each of the first and second pin/rod clamps has an attachment means for attaching to at least one of the following: a frame rod associated with a frame of the fixator and/or a bone pin for implantation in a bone fragment. A clamp screw having an elongated cylindrical threaded body extends through and connecting the first and second pin/rod clamps. The universal clamp apparatus has size changeable knob. The central screw turn actuator engages with the clamp screw to permit rotation of the central screw turn actuator relative to and movement along the cylindrical threaded body when rotational force is applied in first and second rotational directions to the force amplifying knob in order to thereby prevent and permit relative movement, respectively, of a combination of the central screw turn actuator, the first clamp, and the second clamp. The size changeable knob is designed to change between a first size and a second size. The first size has at least a part that extends a greater distance in a direction outwardly from the threaded body of the clamp screw as compared to the second size so that a greater rotational torque can be applied relative to the clamp screw in connection with the first size as compared to the second size.

Other embodiments, among others, are a multipurpose orthopedic external fixator that employs the universal clamp apparatus described in one of the previous two paragraphs.

Other embodiments, among others, are a multipurpose orthopedic external fixator that uses the universal clamp apparatus wherein all parts are made from a glass fiber in order to substantially reduce or prevent magnetically induced current that can result from magnetic resonance imaging (MRI).

Other embodiments, apparatus, methods, features, and advantages of the present invention will be apparent to one with skill in the art upon examination of the following drawings and detailed description. It is intended that all such additional embodiments, apparatus, methods, features, and advantages be included within this disclosure, be within the scope of the present invention, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1A and 1B are perspective views of a multi-purpose external fixator having a first embodiment of the universal clamp apparatus with turn levers in a closed and open position, respectively, in an implementation example with each universal clamp apparatus attached to two frame rods and two bone pins attached to respective bone fragments.

FIG. 2A is a perspective view of the second embodiment of the universal clamp apparatus having first and second clamps and with turn levers in a closed position, in an implementation example with the first clamp attached to two frame rods and the second clamp attached to two bone pins. FIG. 2B and FIG. 2C are perspective views of the second embodiment of the universal clamp apparatus of FIG. 2A, showing the universal clamp apparatus with turn levers in a closed and open position, respectively.

FIGS. 3A-3F show various views of the second embodiment of the universal clamp apparatus of FIG. 2. Specifically, FIG. 3A is a perspective view of the second embodiment with turn levers in a closed position. FIG. 3B is a first side view of the second embodiment with turn levers in a closed position. FIG. 3C is a second side view of the second embodiment with turn levers in a closed position, which is ninety degrees rotated from the first side view along the longitudinal axis of the first embodiment. FIG. 3D is a top view of the second embodiment with turn levers in a closed position. FIG. 3E is a top view of the second embodiment with turn levers in an open position. FIG. 3F is a cross-section view of the second embodiment with turn levers in a closed position.

FIG. 4A is a perspective view of the third embodiment with turn levers in a closed position. FIG. 4B is a perspective view of the third embodiment with turn levers in an open position. FIG. 4C is a top view of the third embodiment with turn levers in a closed position. FIG. 4D is a top view of the third embodiment with turn levers in an open position.

FIG. 5A is a perspective view of the fourth embodiment with turn levers in a closed position. FIG. 5B is a perspective view of the fourth embodiment with turn levers in an open position. FIG. 5C is a top view of the fourth embodiment with turn levers in a closed position. FIG. 5D is a top view of the fourth embodiment with turn levers in an open position.

FIGS. 6A-6D show various views of a fifth embodiment of the universal clamp apparatus. Specifically, FIG. 6A is a perspective view of the fifth embodiment with turn levers in a closed position. FIG. 6B is a perspective view of the fifth embodiment i with turn levers in an open position. FIG. 6C is a top view of the fifth embodiment with turn levers in a closed position. FIG. 6D is a top view of the fifth embodiment with turn levers in an open position.

FIG. 7A is a perspective view of the sixth embodiment with turn levers in a closed position. FIG. 7B is a perspective view of the sixth embodiment with turn levers in an open position. FIG. 7C is a top view of the sixth embodiment i with turn levers n a closed position. FIG. 7D is a top view of the sixth embodiment with turn levers in an open position.

FIG. 8A is a perspective view of the seventh embodiment with turn levers in a closed position. FIG. 8B is a perspective view of the seventh embodiment with turn levers in an open position. FIG. 8C is a top view of the seventh embodiment with turn levers in a closed position. FIG. 8D is a top view of the seventh embodiment with turn levers in an open position.

FIG. 9A is a perspective view of the eighth embodiment. FIG. 9B is a side view of the eighth embodiment. FIG. 9C is a top view of the eighth embodiment.

FIG. 10A is a perspective view of the ninth embodiment in a closed position. FIG. 10B is a perspective view of the ninth embodiment in an open position.

FIGS. 11A-11B show views of a tenth embodiment of the universal clamp apparatus. FIG. 11A is a perspective view of the tenth embodiment with turn levers in a closed position.

FIG. 11B is a perspective view of the tenth embodiment with turn levers in the open position.

DETAILED DESCRIPTION

Figure 1A:
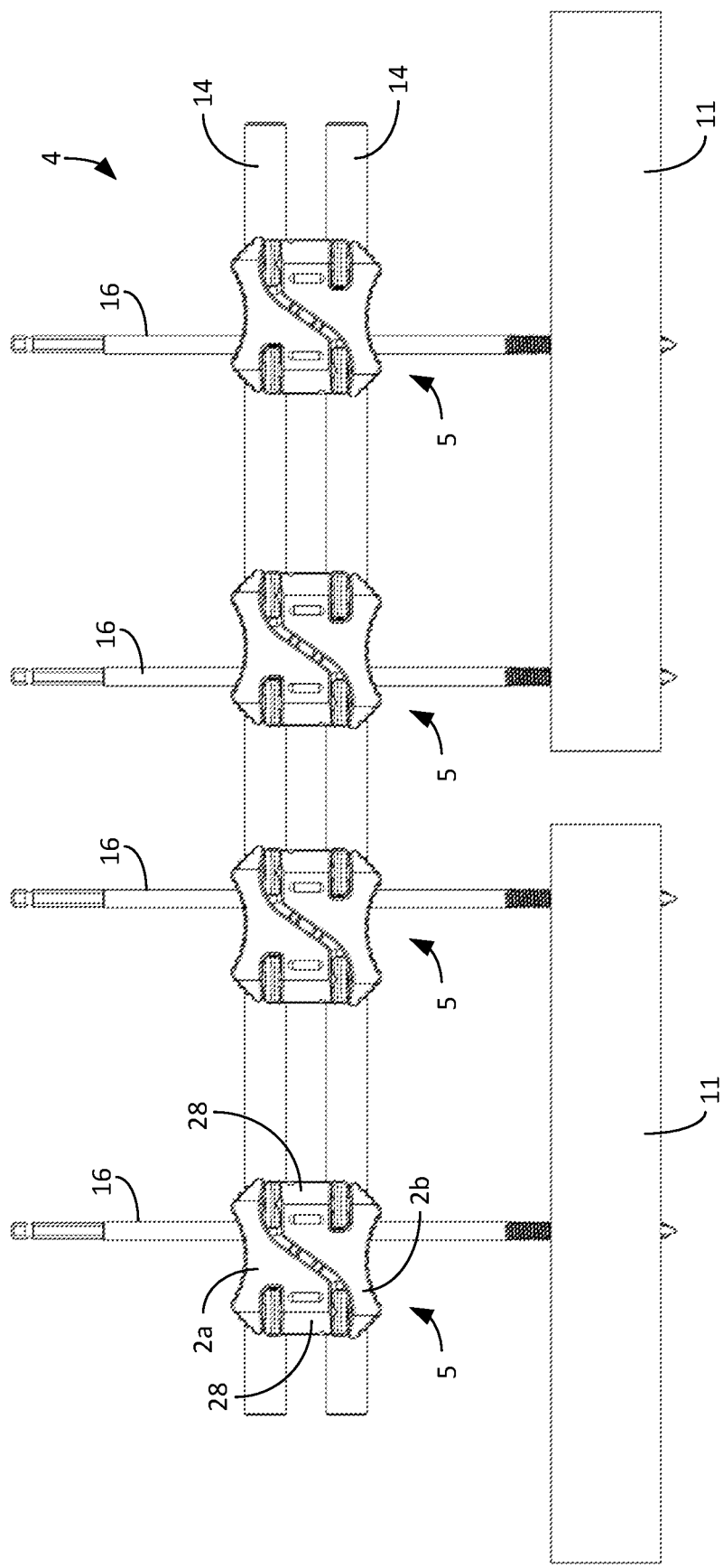
FIGS. 1A and 1B show views of a first embodiment of the universal clamp apparatus. Specifically.
Figure 1B:
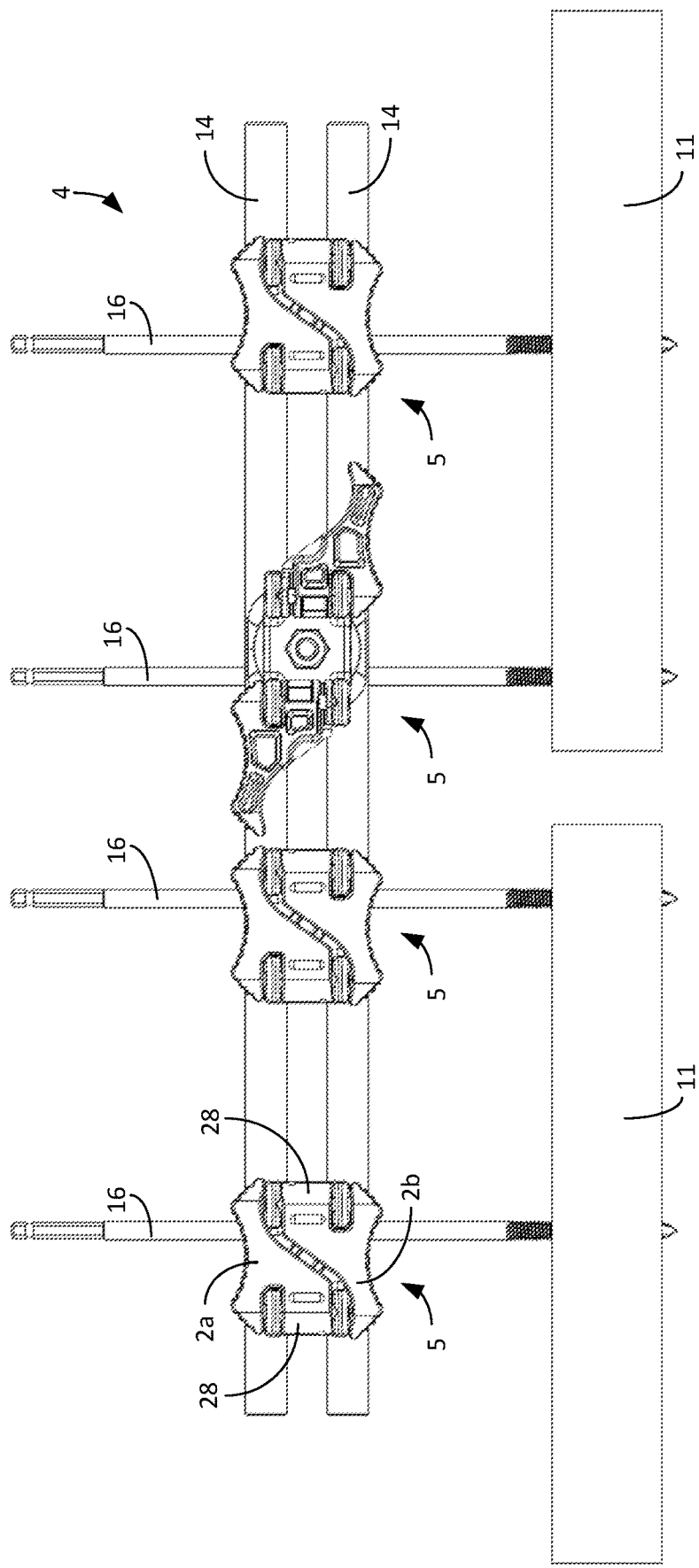

FIGS. 1A and 1B show views of a first embodiment of the universal clamp apparatus for use in a multi-purpose orthopedic external fixator that is used by a doctor for stabilizing a bone fragments associated with a bone fracture(s) in a patient and is generally denoted by reference numeral 5. Specifically, FIGS. 1A and 1B are perspective views of a multi-purpose external fixator 4 having universal clamp apparatus 5 with a torque amplifying knob 15 having collapsible (e.g., foldable), turn levers 2a, 2b in a closed position and an open position, respectively. In this implementation example, as shown in FIGS. 1A and 1B, each universal clamp apparatus 5 is attached to two frame rods 14 and two bone pins 16. Each of the universal clamp apparatus 5 is attached to the frame rods 14 and the bone pins 16 using a clamping mechanism and ratcheting/securing mechanism that is shown in FIGS. 2 and 3 and that will be described in detail hereafter in connection with the second embodiment of the universal clamp apparatus. As further illustrated in FIGS. 1A and 1B, the bone pins 16 are attached to respective bone fragments 9 via threaded ends that are screwed into bone fragments 9. Advantageously, this first embodiment and the remaining embodiments to be described can be operated without the need for tools and with extraordinary tightening precision.

FIGS. 2A-2C and 3A-3F show views of a second embodiment of the universal clamp apparatus and is generally denoted by reference numeral 10. This second embodiment is not a preferred configuration but is merely shown for illustrating how the rods 14 and pins 16 connect to the universal clamp apparatus 10.

The universal clamp apparatus 10 has at least one but preferably two pin/rod clamps 12. In this second embodiment, there are first and second pin/rod clamps 12a, 12b. Each of the first and second pin/rod clamps 12a, 12b, has respective first and second attachment mechanisms (e.g., grooves) for attaching to at least two of the following: a frame rod 14 (e.g., 11 mm rod, 12 mm rod, etc.) associated with a frame of the fixator and/or at least one of a bone pin 16 for implantation in a bone 11. Each pin/rod clamp 12 should enable at least the following attachments: pin 16 to rod 14, rod 14 to rod 14, and pin 16 to pin 16. In this embodiment, there are two seating channels 19 for rods 14 and two seating channels 21 for bone pins 16 in each clamp 12a, 12b.

Figure 2A:
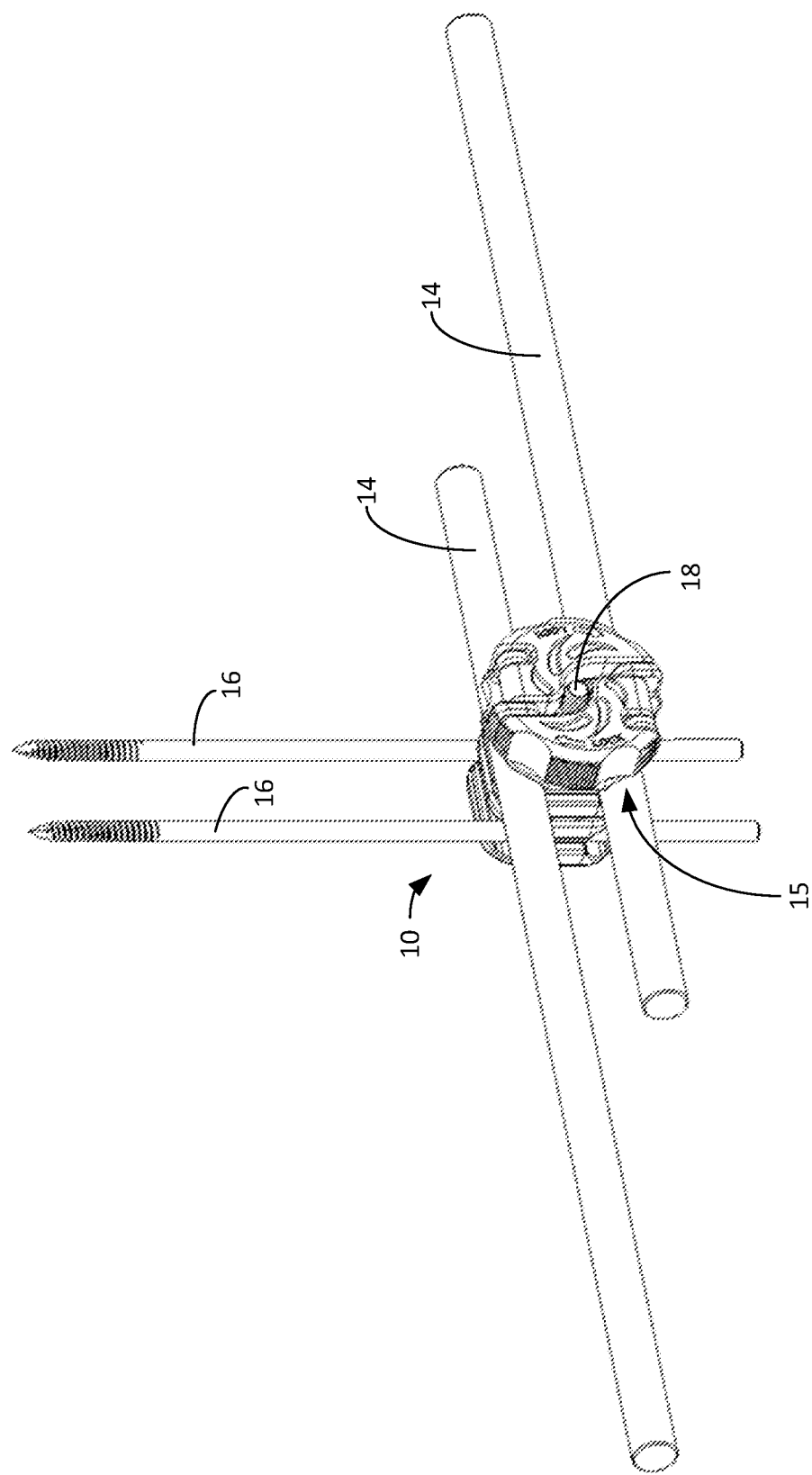
FIGS. 2A-2C show various views of a second embodiment of the universal clamp apparatus. Specifically.
Figure 2B:
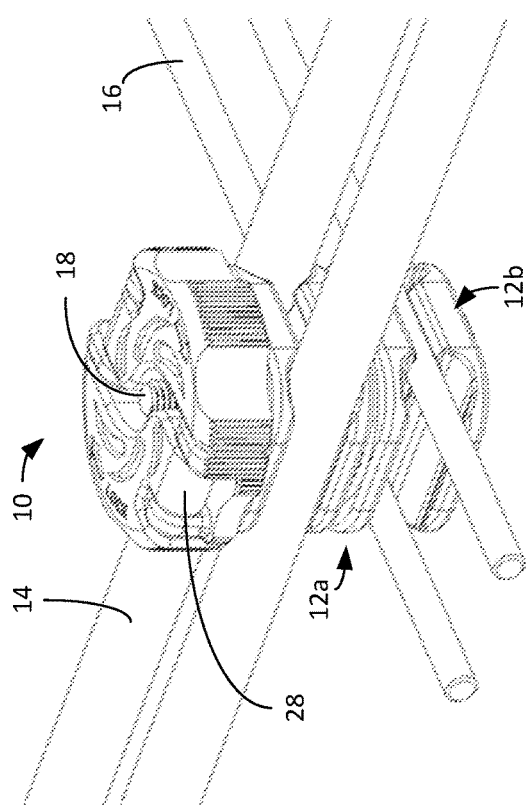
Figure 2C:
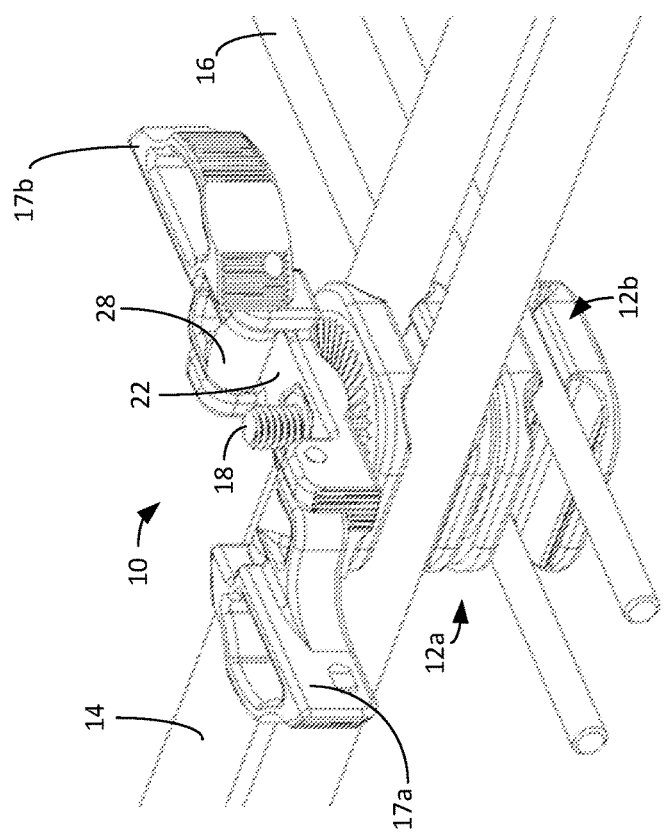

As shown in FIGS. 2A, 2B, and 2C, a frame rod(s) 14 can be situated in, or snapped in, a corresponding seating groove in the first clamp 12a and/or second clamp 12b, and a bone pin(s) 16 can also be situated in, or snapped in, a corresponding seating groove in the first clamp 12a and/or second clamp 12b. In order to tighten them in place, a torque amplifying knob 15 is rotated. Collapsible turn levers 17a, 17b associated with the torque amplifying knob 15 can be un-collapsed, or in this case unfolded, as shown in FIG. 2B to increase torque in order to assist with rotation, and then afterward, collapsed back in place as shown in FIG. 2A to desirably minimize the profile of the torque amplifying knob 15. Each of the levers 17a, 17b are of a size and shape such that when in the collapsed position, each of the levers 17a, 17b substantially and unobtrusively resides within the peripheral edges of the first and second pin/rod clamps 12a, 12b. Generally, the torque amplifying knob 15 is ergonomically shaped in this embodiment as well as the others that will be discussed hereafter.

Each of the first and second pin/rod clamps 12a, 12b comprises a body with generally planar first and second sides and a lateral peripheral edge. Each of the bodies has a screw hole extending through the body between the planar first and second sides. The screw hole has a shape and size to permit passage of a threaded body of a clamp screw 18 therethrough. The bodies of the first and second pin/rod clamps 12a, 12b are generally in parallel. The bodies of the first and second pin/rod clamps 12a, 12b are either fixed relative to or rotatable about a clamp screw 18 based upon a longitudinal location of the torque amplifying knob along the threaded body of a clamp screw 18. The peripheral edge has longitudinal seating channels 19, 21 along the edge. Each of the seating channels 19, 21 has a longitudinal channel opening with a shape and size to receive and permit entry of either a rod 14 or a bone pin 16 therein. The first and second pin/rod clamps 12a, 12b are made from a material, for example but not limited to, plastic, that has sufficient rigidly and sufficient flexibility so that a rod 14 or bone pin 16 can be snapped into and out of the respective channels 19, 21, and so that when the pin/rod clamps 12a, 12b are squeezed and un-squeezed, the rod 14 or bone pin 16 is secured or un-secured within the seating channels 19, 21 by slight flexing, or movement, of the curved side walls defining the seating channels 19, 21.

Preferably, to achieve a more universal device, each of the first and second attachment mechanisms associated with each of the first and second pin/rod clamps 12a, 12b comprise two opposing seating channels 19 for rods 14 on opposing ends of the peripheral edge and two opposing seating channels 21 designed for bone pins 16 on opposing ends of the peripheral edge.

The universal clamp apparatus 10 preferably but optionally employs a ratcheting and securing mechanism to assist in securing the relationship between the pin/rod clamps 12a, 12b. More specifically, the planar side of the first clamp 12a that is contiguous with the planar side of the second clamp 12b has radial ratchet grooves 23 situated symmetrically about the clamp screw hole that, in effect, implement a ratcheting and securing mechanism. These radial ratchet grooves 23 of the first clamp 12a are in mating engagement with these radial ratchet grooves 23 of the second clamp 12b so that the rotation of the first and second pin/rod clamps 12a, 12b occurs in discrete rotational steps. In this embodiment, it was convenient for manufacturing (but not necessary) that the planar first and second sides of the body of the pin/rod clamps 12a, 12b each comprise radial ratchet grooves 23.

The clamp screw mechanism comprises an elongated cylindrical threaded body extending through and connecting the first and second pin/rod clamps 12a, 12b. A central screw turn actuator 22 is connected to a clamp screw nut 24. The clamp screw 18 extends through the first and second pin/rod clamps 12a, 12b, and an underside of a clamp screw head 26 is contiguous with a planar side of the second clamp 12b. In the preferred embodiment, the clamp screw 18 is a lock screw, but other screw types are possible. In an alternative embodiment, the clamp screw nut 24 and the central screw turn actuator 22 can be singular unitary part. In another alternative embodiment, the clamp screw head 26 could be situated at the central turn actuator 22 and the nut 24 situated at the planar side of the second clamp 12b.

The torque amplifying knob 15 has a plurality of collapsible turn levers 17a, 17b. Each lever 17a, 17b has a longitudinal body extending between a movable end and a hinged end. The hinged end is connected via a hinge 28 to the central screw turn actuator 22. The movable end is movable between a collapsed position where the movable end is situated over the central screw turn actuator 22 and an open position where the movable end is situated outwardly from the central screw turn actuator 22. The central screw turn actuator 22 engages with the clamp screw 18 to cause rotation of the central screw turn actuator 22 relative to and movement along the cylindrical threaded body when rotational force is applied in first and second rotational directions to either (a) the torque amplifying knob 15 in a closed position or (b) the levers 17a, 17b when the levers 17a, 17b are in the open position, in order to thereby prevent and permit relative movement, respectively, of a combination of the central screw turn actuator, the first clamp 12a, and the second clamp 12b.

As illustrated in FIG. 3E, optionally, a spring 31 is implemented between the pin/rod clamps 12a, 12b in order to impose a separation force between the pin/rod clamps 12a, 12b. This feature, along with the radial ratchet grooves 23 that are in physical contact, assists with effecting a ratcheting and securing effect when the wig torque amplifying knob 15 is rotated.

The following discussion focuses on third through tenth embodiments of the universal clamp apparatus. These embodiments have a similar architecture and parts as the first and second embodiments. Generally, the clamping mechanism and the ratcheting/securing mechanism, which includes the first and second pin/rod clamps 12a, 12b, the screw 18, spring 31, and radial ratchet grooves are substantially the same in these embodiments. Moreover, the torque amplifying knobs (including central screw turn actuator and turn lever(s)) are different in appearance and have different ergonomics, as is illustrated in FIGS. 4 through 11).

Figure 4B:
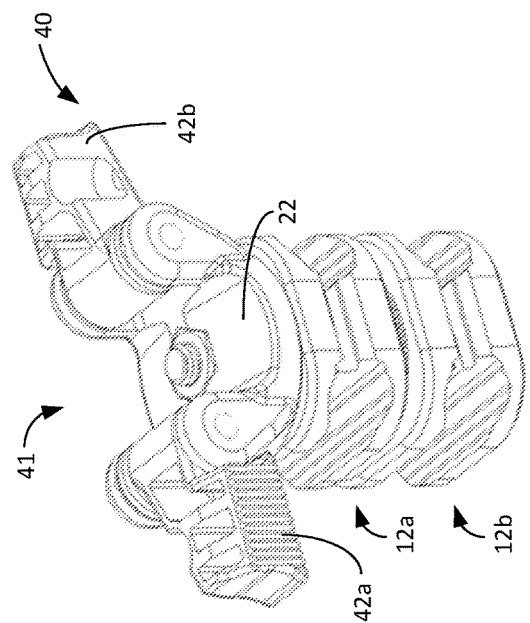
FIGS. 4A-4D show various views of a third embodiment of the universal clamp apparatus. Specifically.
Figure 4D:
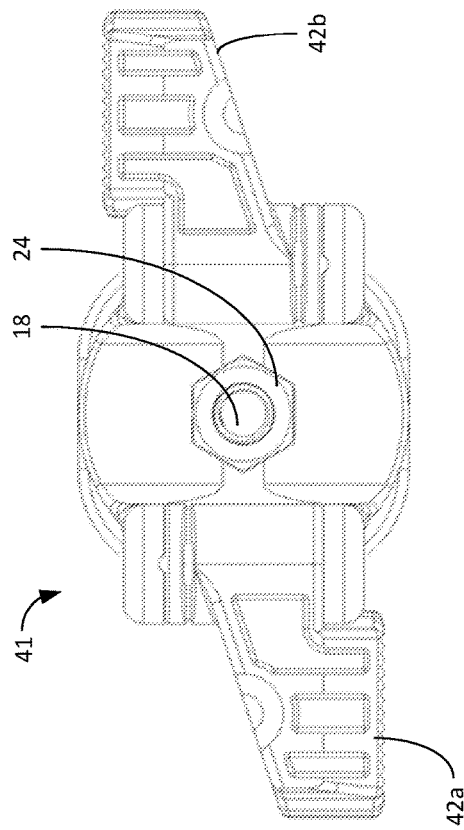
Figure 4A:
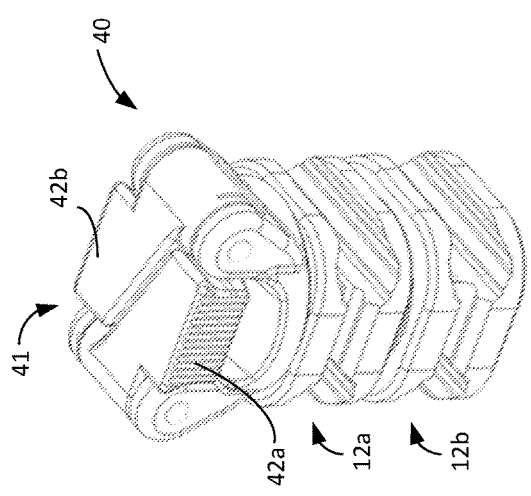
Figure 4C:
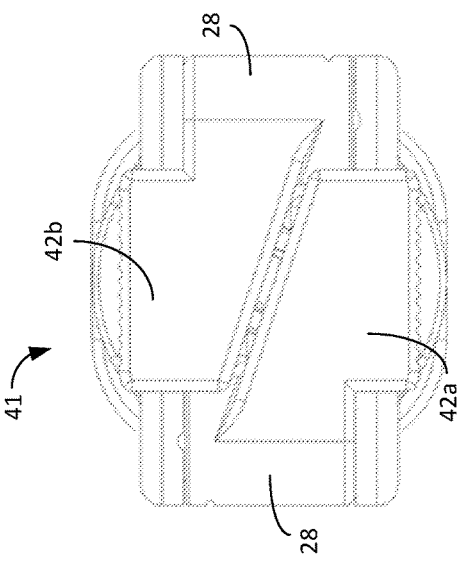

More specifically, FIGS. 4A-4D show various views of a third embodiment of the universal clamp apparatus and is generally denoted by reference numeral 40. Specifically, FIG. 4A is a perspective view of the universal clamp apparatus 40 with an ergonomic torque amplifying knob 41 having collapsible turn levers 42a, 42b in a closed position. FIG. 4B is a perspective view of the universal clamp apparatus 40 with torque amplifying knob 41 having levers 42a, 42b in an open position. FIG. 4C is a top view of the universal clamp apparatus 40 with torque amplifying knob 41 having levers 42a, 42b in a closed position. FIG. 4D is a top view of the universal clamp apparatus 40 with torque amplifying knob 41 having levers 42a, 42b in an open position.

Figure 5A:
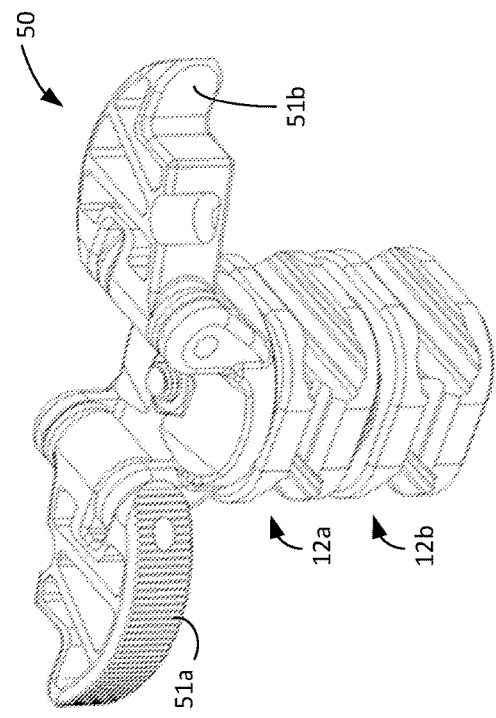
FIGS. 5A-5D show various views of a fourth embodiment of the universal clamp apparatus. Specifically.
Figure 5C:
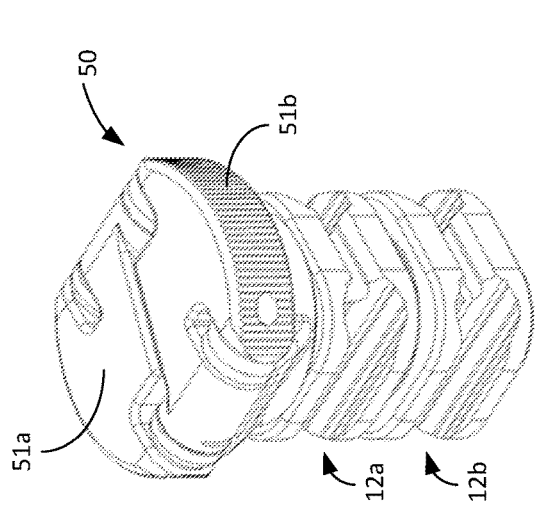
Figure 5B:
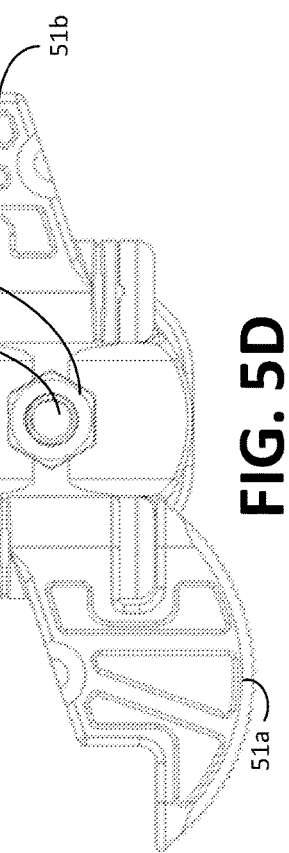
Figure 5D:
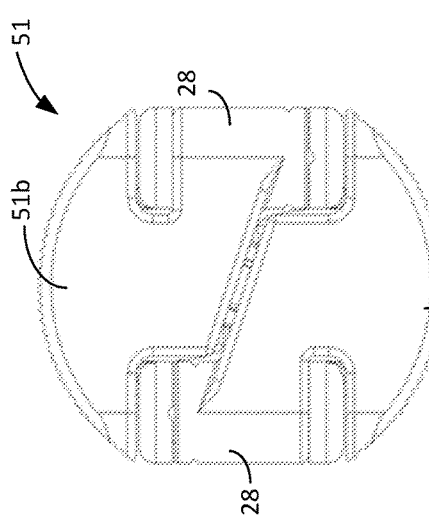

FIGS. 5A-5D show various views of a fourth embodiment of the universal clamp apparatus and is generally denoted by reference numeral 50. Specifically, FIG. 5A is a perspective view of the universal clamp apparatus 50 with t an ergonomic torque amplifying knob 51 having collapsible turn levers 52a, 52b in a closed position. FIG. 5B is a perspective view of the universal clamp apparatus 50 with torque amplifying knob 51 having collapsible turn levers 52a, 52b in an open position. FIG. 5C is a top view of the universal clamp apparatus 50 with torque amplifying knob 51 having collapsible turn levers 52a, 52b in a closed position. FIG. 5D is a top view of the universal clamp apparatus 50 with torque amplifying knob 51 having the collapsible turn levers 52a, 52b in an open position.

FIGS. 6A-6D show various views of a fifth embodiment of the universal clamp apparatus and is generally denoted by reference numeral 60. Specifically, FIG. 6A is a perspective view of the universal clamp apparatus 60 with an ergonomic torque amplifying knob 61 having collapsible turn levers 62a, 62b in a closed position. FIG. 6B is a perspective view of the universal clamp apparatus 60 with torque amplifying knob 61 having collapsible turn levers 62a, 62b in an open position. FIG. 6C is a top view of the universal clamp apparatus 60 with torque amplifying knob 61 having collapsible turn levers 62a, 62b in a closed position. FIG. 6D is a top view of the universal clamp apparatus 60 with torque amplifying knob 61 having collapsible turn levers 62a, 62b in an open position.

Figure 7B:
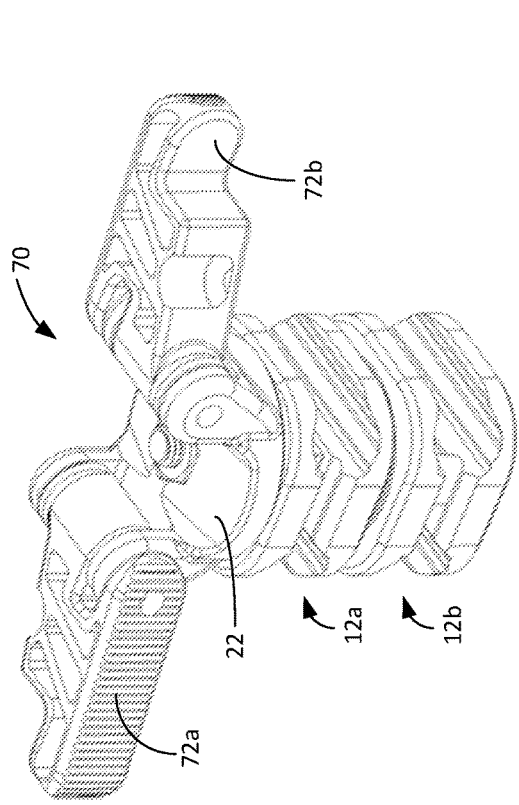
FIGS. 7A-7D show various views of a sixth embodiment of the universal clamp apparatus. Specifically.
Figure 7D:
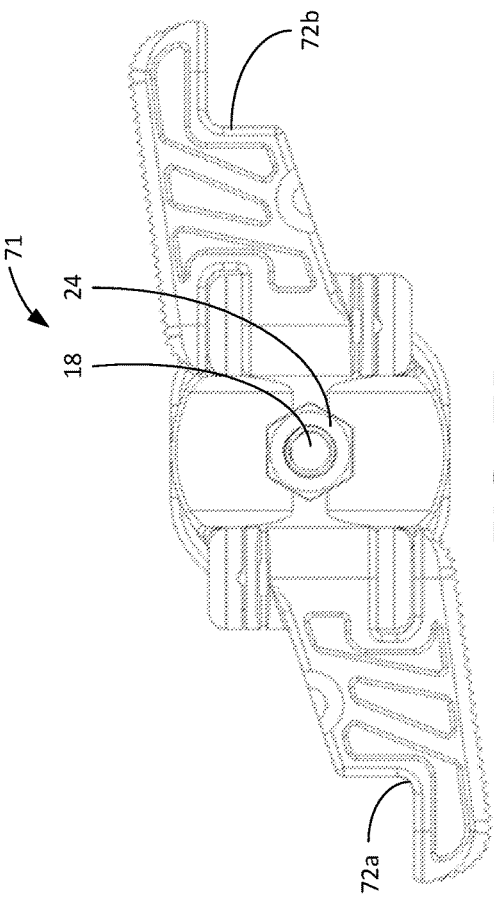
Figure 7A:
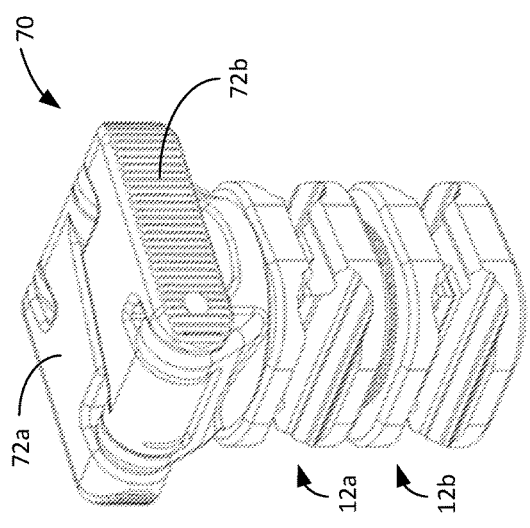
Figure 7C:
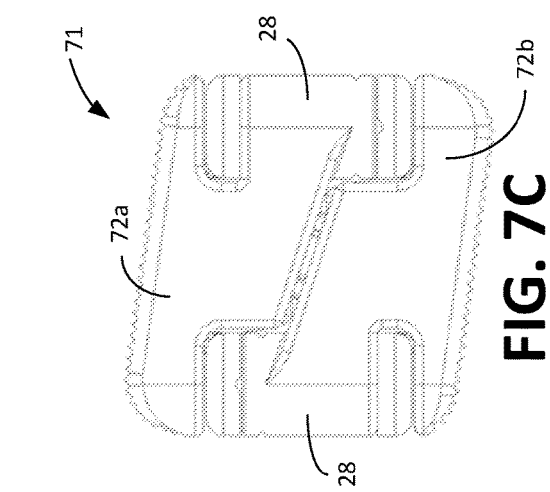

FIGS. 7A-7D show various views of a sixth embodiment of the universal clamp apparatus and is generally denoted by reference numeral 70. Specifically, FIG. 7A is a perspective view of the universal clamp apparatus 70 with an ergonomic torque amplifying knob 71 having collapsible turn levers 72a, 72b in a closed position. FIG. 7B is a perspective view of the universal clamp apparatus 70 with torque amplifying knob 71 having collapsible turn levers 72a, 72b in an open position. FIG. 7C is a top view of the universal clamp apparatus 70 with torque amplifying knob 71 having collapsible turn levers 72a, 72b in a closed position. FIG. 7D is a top view of the universal clamp apparatus 70 with torque amplifying knob 71 having collapsible turn levers 72a, 72b in an open position.

Figure 8B:
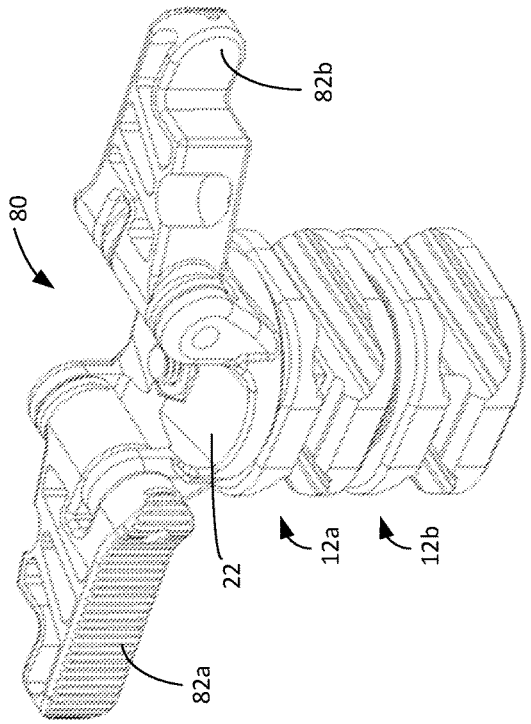
FIGS. 8A-8D show various views of a seventh embodiment of the universal clamp apparatus. Specifically.
Figure 8A:
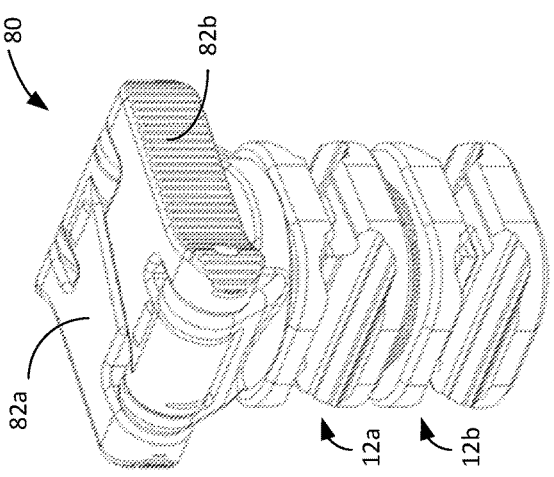
Figure 8D:
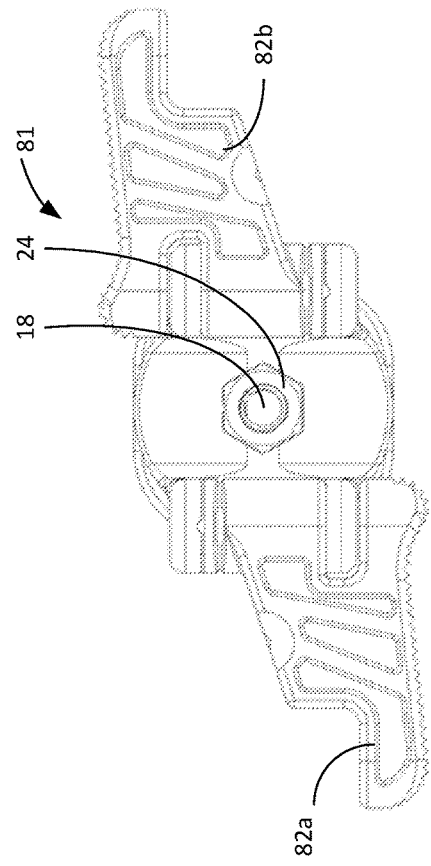
Figure 8C:
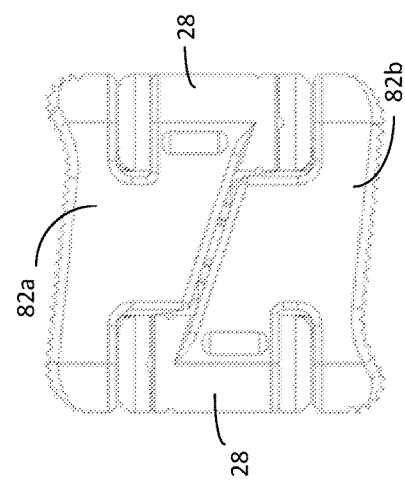

FIGS. 8A-8D show various views of a seventh embodiment of the universal clamp apparatus and is generally denoted by reference numeral 80. Specifically, FIG. 8A is a perspective view of the universal clamp apparatus 80 with an ergonomic torque amplifying knob 81 having collapsible turn levers 82a, 82b in a closed position. FIG. 8B is a perspective view of the universal clamp apparatus 80 with torque amplifying knob 81 having collapsible turn levers 82a, 82b in an open position. FIG. 8C is a top view of the universal clamp apparatus 80 with torque amplifying knob 81 having collapsible turn levers 82a, 82b in a closed position. FIG. 8D is a top view of the universal clamp apparatus 80 with torque amplifying knob 81 having collapsible turn levers 82a, 82b in an open position.

Figure 9A:
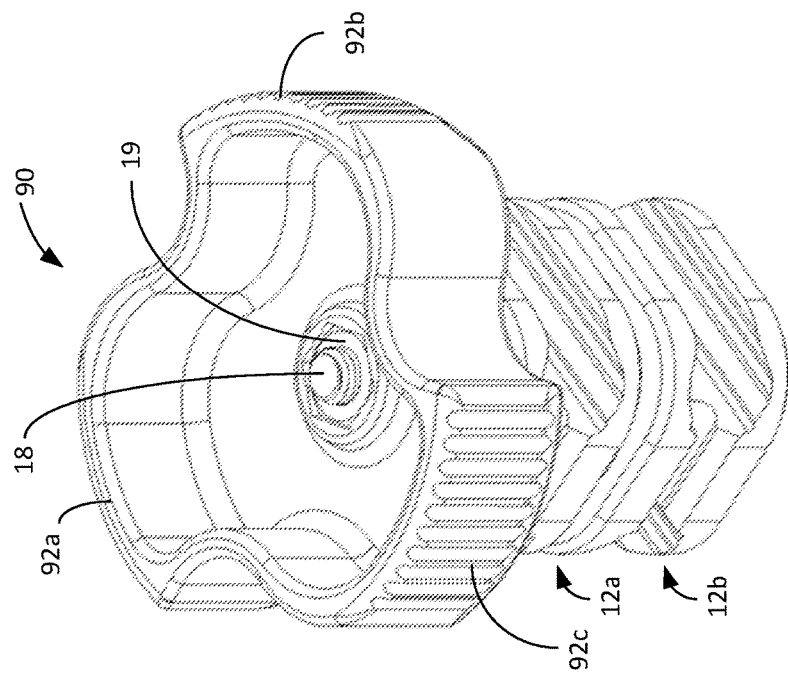
FIGS. 9A-9C show various views of an eighth embodiment of the universal clamp apparatus wherein the clamp employs a knob having a plurality of fixed levers. Specifically.
Figure 9B:
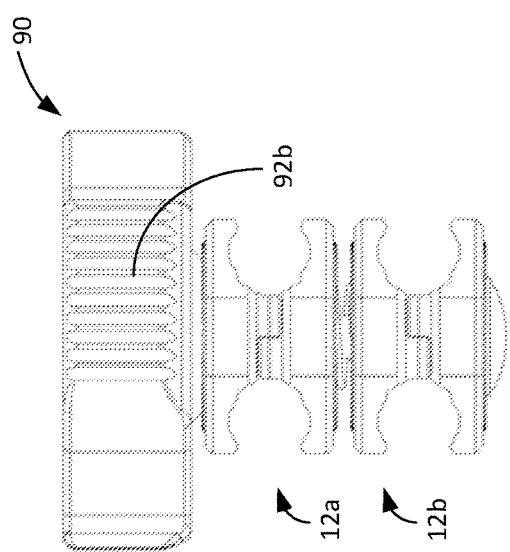
Figure 9C:
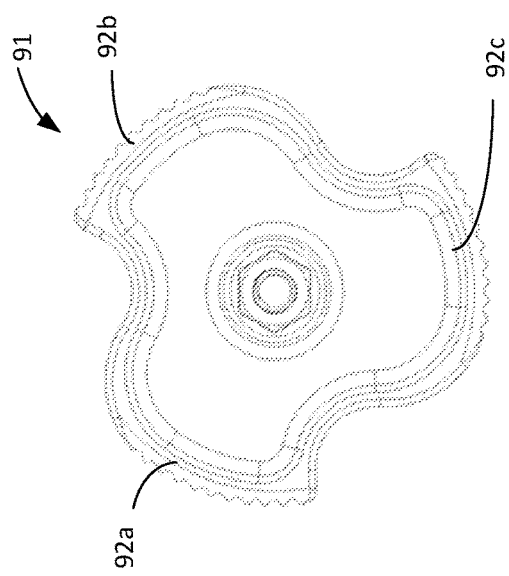

FIGS. 9A-9C show various views of an eighth embodiment of the universal clamp apparatus and is generally denoted by reference numeral 90. In the universal clamp apparatus 90, the clamp 90 does not employ collapsible turn levers, but instead employs an ergonomic torque amplifying knob 91 having one or more, but preferably a plurality, of non-collapsible fixed levers 92 extending outwardly from a central part of the torque amplifying knob 91. In this universal clamp apparatus 90 of this eighth embodiment, there are three levers 92a, 92b, 92c, which is the preferred design. In this eighth embodiment, these turn levers 92 are shaped and sized so that the overall profile of the torque amplifying knob 91 extends only minimally from the periphery. FIG. 9A is a perspective view of the eighth embodiment. FIG. 9B is a side view of the universal clamp apparatus 90. FIG. 9C is a top view of the universal clamp apparatus 90. In the universal clamp apparatus 90, there is no separate central screw turn actuator 22, as with the other embodiments. The torque amplifying knob 91 is secured to and directly rotates the nut about the threaded body of the screw 18. The torque amplifying knob 91 serves as the central screw turn actuator 22. Furthermore, the threaded nut and the torque amplifying knob can be a singular unitary part, if desired. When operated, the torque amplifying knob 91 engages the clamp screw mechanism to cause movement of the torque amplifying knob 91 along the cylindrical threaded body when rotational force is applied in first and second rotational directions to the torque amplifying knob 91 in order to thereby prevent and permit relative movement, respectively, of the torque amplifying knob 91 and the pin/rod clamps 12a, 12b.

In an alternative embodiment, the knob 91 has only one lever 92a extending outwardly from a generally circular central knob 91 that also serves as the screw turn actuator. In yet another alternative embodiment, the knob 91 has only two levers 92, preferably extending outwardly in opposing directions from a generally circular central knob 91 that also serves as the screw turn actuator.

Figures 10A, 10B:
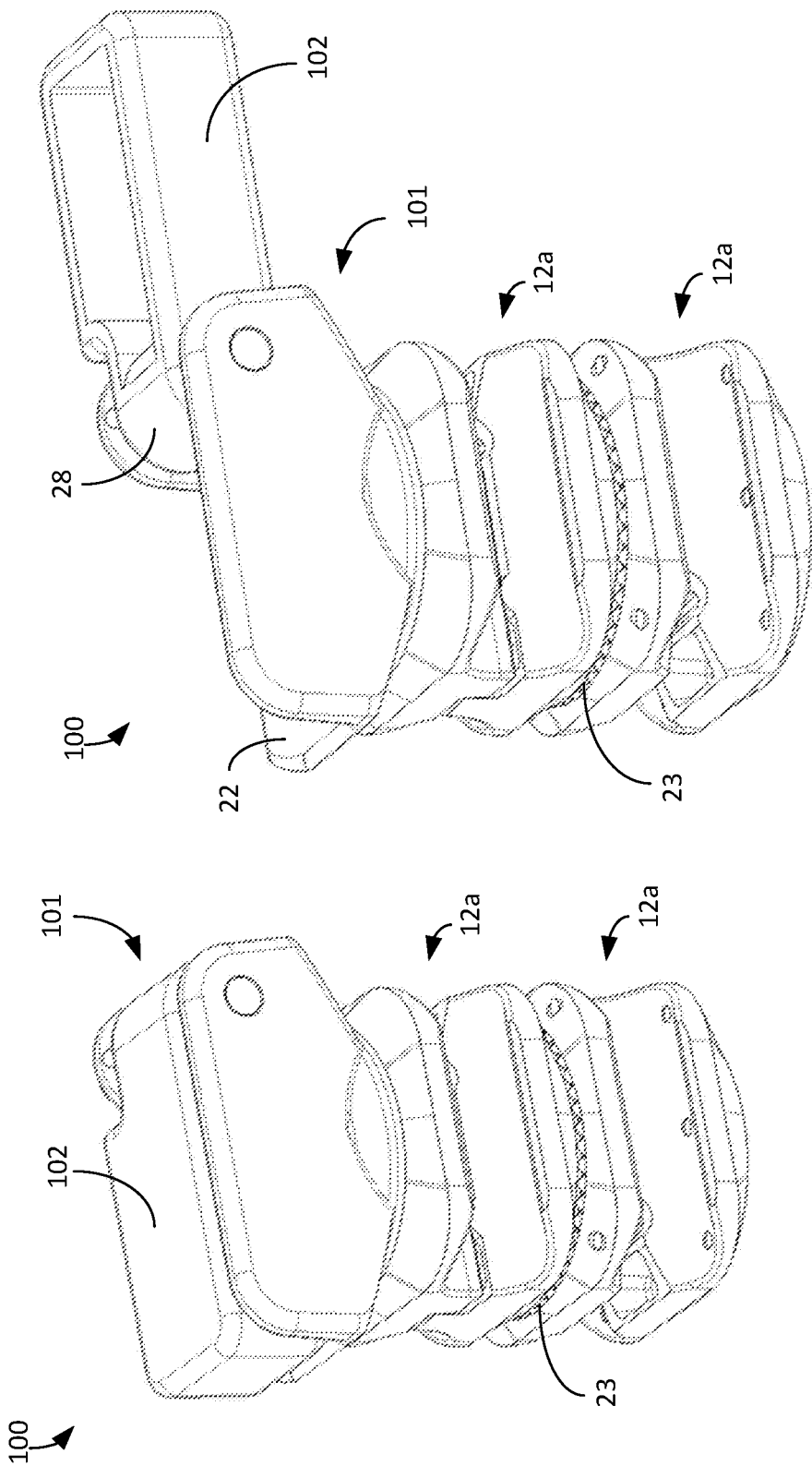
FIGS. 10A-10B show views of a ninth embodiment of the universal clamp apparatus wherein the clamp employs a single turn lever. Specifically.

FIGS. 10A-10B views of a ninth embodiment of the universal clamp apparatus and is generally denoted by reference numeral 100. In this ninth embodiment, the universal clamp apparatus 100 employs an ergonomic torque amplifying knob 101 with a collapsible single turn lever 102. Specifically, FIG. 10A is a perspective view of the ninth embodiment in a closed position. FIG. 10B is a perspective view of the ninth embodiment in an open position.

FIGS. 11A-11B show a perspective view of a tenth embodiment of the universal clamp apparatus and is generally denoted by reference numeral 110. FIG. 11A is a perspective view of the tenth embodiment with torque amplifying knob 111 having collapsible turn levers 112a, 112b in a closed position. FIG. 11B is a perspective view of the tenth embodiment with the collapsible turn levers 112a, 112b of the knob 11 in the open position. As shown, in this tenth embodiment, the collapsible turn levers 112a, 112b are not connected to the screw turn actuator 22 via hinges 28 but instead slide or collapse in and out of a channel within the screw turn actuator 22 in order to put them in the closed position and the open position, respectively.

The multipurpose orthopedic external fixator that uses any of the foregoing embodiments of the universal clamp apparatus can be constructed from numerous possible materials. However, in the preferred embodiments, in order to reduce or prevent magnetically induced current that can result from magnetic resonance imaging (MRI) (and that results in undesirable heat), all the parts (pin/rod clamps, clamp screw, torque amplifying knob, etc.) are made from a glass fiber.

Although the preferred embodiments of the universal clamp apparatus have two pin/rod clamps 12a, 12b, it is possible to construct a universal clamp apparatus with only a single clamp with any combination of rod and bone screw seating channels 19, 21, or a universal clamp apparatus with more than two pin/rod clamps with any combination of frame rod and/or bone screw seating channels 19, 21.

Moreover, although the preferred embodiments of each clamp 12a, 12b has two seating channels 19 for respective rods 14 and two seating channels 16 for respective bone pins 16, each clamp 12a, 12b can be constructed with: (a) merely two rod channels 19, (b) merely two bone pin channels 21, or (c) merely one rod channel 19 and one bone pin channel 21.

Finally, it should be emphasized that the above-described embodiments of the present invention, particularly, any "preferred" embodiments, are merely possible nonlimiting examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention.

At least the following is claimed:

1. A universal clamp apparatus for an orthopedic external fixator, the universal clamp apparatus comprising:

first and second pin/rod clamps, each of the first and second pin/rod clamps having an attachment means for attaching to at least one of the following: a frame rod associated with a frame of the fixator and/or a bone pin for implantation in a bone fragment;

a clamp screw comprising an elongated cylindrical threaded body extending through and connecting the first and second pin/rod clamps, the threaded body extending along a screw axis;

a torque amplifying knob, the knob having a plurality of collapsible turn levers, each turn lever having a longitudinal body extending between a movable end and a hinged end, the knob having a central screw turn actuator with an outer side and an inner side, the hinged end of each turn lever being connected via a hinge to the outer side of the central screw turn actuator, the movable end of each turn lever being movable between a collapsed position where each lever is situated over the outer side of the central screw turn actuator and an open position where the movable end is situated outwardly from the outer side of the central screw turn actuator, the central screw turn actuator engaged with the clamp screw to permit rotation of the central screw turn actuator relative to and movement along the cylindrical threaded body when rotational force is applied in first and second rotational directions to the torque amplifying knob in order to permit relative movement of the first clamp and the second clamp;

wherein each hinge pivots about a hinge longitudinal body, the hinge longitudinal bodies;

being parallel to one another, being substantially coextensive along the outer side of the central screw turn actuator, and extending perpendicular to the clamp screw, the screw axis being generally centered between the substantially coextensive hinge longitudinal bodies;

wherein the turn levers are collapsed in a side-by-side arrangement; and wherein each of the longitudinal bodies of the turn levers have inner and outer edges, the inner edges being closer to the screw axis than the outer edges, the inner edges having respective contours that engage in a mating complimentary manner when the turn levers are collapsed in the side-by-side arrangement, the longitudinal bodies having sufficient size to cover a substantial part of the outer side of the central screw turn actuator when the turn levers are collapsed.

2. The universal clamp apparatus of claim 1, wherein each of the first and second pin/rod clamps comprise a body with generally planar first and second sides and a lateral peripheral edge, each of the bodies having a screw hole extending through the body between the planar first and second sides, the screw hole having a shape and size to permit passage of the threaded body of the clamp screw therethrough, the planar sides of the bodies of the first and second pin/rod clamps being in parallel, the bodies of the first and second pin/rod clamps being either fixed relative to or rotatable about the clamp screw based upon a longitudinal location of the torque amplifying knob along the threaded body of the clamp screw, the peripheral edge having longitudinal seating channels along the edge, each of the channels having a channel opening with a shape and size to receive and permit entry of either a rod or a bone pin therein.

3. The universal clamp apparatus of claim 2, wherein each of the attachment means associated with each of the first and second pin/rod clamps comprises two opposing and parallel seating channels for rods at opposing ends of the peripheral edge and two opposing and parallel seating channels for bone pins at opposing ends of the peripheral edge.

4. The universal clamp apparatus of claim 2, wherein a planar side of the first clamp that is contiguous with a planar side of the second clamp has radial ratchet grooves situated about the clamp screw hole that implement a ratcheting and securing mechanism, the ratchet grooves of the first clamp being in mating engagement with the ratchet grooves of the second clamp so that the rotation of the first and second pin/rod clamps occurs in discrete incremental rotational steps.

5. The universal clamp apparatus of claim 4, further comprising a spring situated between the first and second pin/rod clamps that imposes a separation force between the first and second pin/rod clamps that, along with the radial ratchet grooves that are in physical contact, assists with effecting a ratcheting and securing effect when the knob is rotated.

6. The universal clamp apparatus of claim 2, wherein the clamp screw further comprises a clamp screw head and a threaded nut of a shape and size to move along the threaded body, and wherein the central screw turn actuator is connected to the clamp screw nu, and an underside of the clamp screw head is secured to the one of the first and second pin/rod clamps that is furthest away from the central screw turn actuator.

7. The universal clamp apparatus of claim 2, wherein each of the turn levers of the torque amplifying knob are of a size and shape such that when in the collapsed position, each of the turn levers substantially resides within the peripheral edges of the first and second pin/rod clamps.

8. The universal clamp apparatus of claim 7, wherein the threaded nut and the central screw turn actuator are a singular unitary part.

9. A multi-purpose external fixator, comprising the universal clamp apparatus of claim 1.

10. The external fixator of claim 9, wherein the pin/rod clamps, the clamp screw, and the torque amplifying knob are made with a glass fiber.

11. A universal clamp apparatus for an orthopedic external fixator, the universal clamp apparatus comprising:
first and second pin/rod clamps, each of the first and second pin/rod clamps having an attachment means for attaching to at least one of the following: a frame rod associated with a frame of the fixator and/or a bone pin for implantation in a bone fragment;
a clamp screw comprising an elongated cylindrical threaded body extending along a screw axis through and connecting the first and second pin/rod clamps;
a size changeable knob designed to change between a first size and a second size, the first size having at least a part that extends a greater distance in a direction outwardly from the threaded body of the clamp screw as compared to the second size so that a greater rotational torque can be applied relative to the clamp screw in connection with the first size as compared to the second size, the knob having a central screw turn actuator engaged with the clamp screw to permit rotation of the central screw turn actuator relative to and movement along the cylindrical threaded body when rotational force is applied in first and second rotational directions to the force amplifying knob in order to permit relative movement of the first pin/rod clamp and the second pin/rod clamp;
wherein the size changeable knob includes one or more collapsible turn levers, each turn lever having a longitudinal body extending between a movable end and a hinged end, the central screw turn actuator having an outer side and an inner side, the hinged end being connected via a hinge to the outer side of the central screw turn actuator, the movable end being movable between a collapsed position where the movable end is situated over the outer side of the central screw turn actuator and an open position where the movable end is situated outwardly from the outer side of the central screw turn actuator;
wherein each hinge pivots about a hinge longitudinal body, the hinge longitudinal body extending perpendicular to the clamp screw;
wherein an axis that is perpendicular to and extends through the screw axis also extends through a central part of the hinge longitudinal body of each hinge; and
wherein each longitudinal body of each turn lever has inner and outer edges, the inner edge being closer to the screw axis than the outer edge, the longitudinal body having sufficient size to cover a substantial part of the outer side of the central screw turn actuator when the one or more turn levers are collapsed.

12. The universal clamp apparatus of claim 11, wherein each of the first and second pin/rod clamps comprise a body with generally planar first and second sides and a lateral peripheral edge, each of the bodies having a screw hole extending through the body between the planar first and second sides, the screw hole having a shape and size to permit passage of the threaded body of the clamp screw therethrough, the planar sides of the bodies of the first and second pin/rod clamps being in parallel, the bodies of the first and second pin/rod clamps being either fixed relative to or rotatable about the clamp screw based upon a longitudinal location of the torque amplifying knob along the threaded body of the clamp screw, the peripheral edge having longitudinal seating channels along the edge, each of the channels having a channel opening with a shape and size to receive and permit entry of either a rod or a bone pin therein.

13. The universal clamp apparatus of claim 11, wherein each of the attachment means associated with each of the first and second pin/rod clamps comprises two opposing and parallel seating channels for rods at opposing ends of the peripheral edge and two opposing and parallel seating channels for bone pins at opposing ends of the peripheral edge.

14. The universal clamp apparatus of claim 13, wherein a planar side of the first clamp that is contiguous with a planar side of the second clamp has radial ratchet grooves situated about the clamp screw hole that implement a ratcheting and securing mechanism, the ratchet grooves of the first clamp being in mating engagement with the ratchet grooves of the second clamp so that the rotation of the first and second pin/rod clamps occurs in discrete incremental rotational steps.

15. The universal clamp apparatus of claim 13, further comprising a spring situated between the first and second pin/rod clamps that imposes a separation force between the first and second pin/rod clamps that, along with the radial ratchet grooves that are in physical contact, assists with effecting a ratcheting and securing effect when the knob is rotated.

16. The universal clamp apparatus of claim 13, wherein the clamp screw further comprises a clamp screw head and a threaded nut of a shape and size to move along the threaded body, and wherein the central screw turn actuator is connected to the clamp screw nu, and an underside of the clamp screw head is secured to the one of the first and second pin/rod clamps that is furthest away from the central screw turn actuator.

17. The universal clamp apparatus of claim 13, wherein each of the turn levers of the knob are of a size and shape such that when in the collapsed position, each of the turn levers substantially resides within the peripheral edges of the first and second pin/rod clamps.

18. The universal clamp apparatus of claim 16, wherein the threaded nut and the central screw turn actuator are a singular unitary part.

19. A multi-purpose external fixator, comprising the universal clamp apparatus of claim 16.

20. A universal clamp apparatus for an orthopedic external fixator, the universal clamp apparatus comprising:
   first and second pin/rod clamps, each of the first and second pin/rod clamps having an attachment means for attaching to at least one of the following: a frame rod associated with a frame of the fixator and/or a bone pin for implantation in a bone fragment;
   a clamp screw comprising an elongated cylindrical threaded body extending along a screw axis through and connecting the first and second pin/rod clamps;
   a torque amplifying knob, the knob having a plurality of collapsible turn levers, each turn lever having a longitudinal body extending between a movable end and a hinged end, the knob having a central screw turn actuator with an outer side and an inner side, the hinged end of each the turn lever being connected via a hinge to the outer side of the central screw turn actuator, the movable end of each turn lever being movable between a collapsed position where each lever is situated over the outer side of the central screw turn actuator and an open position where the movable end is situated outwardly from the outer side of the central screw turn actuator, the central screw turn actuator engaged with the clamp screw to permit rotation of the central screw turn actuator relative to and movement along the cylindrical threaded body when rotational force is applied in first and second rotational directions to the torque amplifying knob in order to permit relative movement the first clamp and the second clamp;
   wherein each hinge pivots about a hinge longitudinal body, the hinge longitudinal bodies being parallel to one another and extending perpendicular to the clamp screw
   wherein an axis that is perpendicular to and extends through the screw axis also extends through a central part of the hinge longitudinal body of each hinge; and
   wherein each of the longitudinal bodies of the turn levers have inner and outer edges, the inner edges being closer to the screw axis than the outer edges, the longitudinal bodies having sufficient size to cover a substantial part of the outer side of the central screw turn actuator when the turn levers are in the collapsed position.

* * * * *